United States Patent [19]

Honig et al.

[11] 3,956,431
[45] May 11, 1976

[54] PROCESS FOR FORMING PHOSPHONATE POLYMERS

[75] Inventors: Milton L. Honig, New York; Edward D. Weil, Hastings-on-Hudson, both of N.Y.

[73] Assignee: Stauffer Chemical Company, Westport, Conn.

[22] Filed: June 10, 1974

[21] Appl. No.: 477,873

[52] U.S. Cl. .............................. 260/971; 260/2 P; 260/47 P; 260/79; 260/928; 260/929; 260/930; 526/14; 526/54; 526/278
[51] Int. Cl.² .................... C07F 9/141; C08G 79/04
[58] Field of Search .................. 260/2 P, 80 PS, 79, 260/47 P, 971, 928, 929, 930

[56] References Cited
UNITED STATES PATENTS

| | | | |
|---|---|---|---|
| 2,891,915 | 6/1959 | McCormack et al. | 260/2 P |
| 3,298,967 | 1/1967 | Mason | 260/2 P |

FOREIGN PATENTS OR APPLICATIONS

| | | | |
|---|---|---|---|
| 945,047 | 12/1963 | United Kingdom | 260/2 P |

*Primary Examiner*—Wilbert J. Briggs, Sr.
*Attorney, Agent, or Firm*—Richard P. Fennelly

[57] ABSTRACT

A process is disclosed for forming polymers and oligomers containing the repeating unit

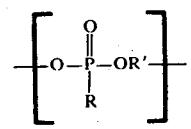

where R is selected from the group consisting of hydrogen and hydrocarbyl, preferably $C_1$-$C_4$ alkyl groups, e.g., methyl and ethyl, and R' is an alkylene group, e.g., a $C_2$-$C_4$ alkylene group, a substituted alkylene group, or an alkylene group having one or more O, S, arylene or vinylene group interruptions in its aliphatic chain. It comprises the transalkylation of a dihalide compound of the formula:

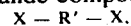

where R' has the same meaning given above and X is either chlorine or bromine and is attached to the terminal carbon atoms in R', with a phosphonate compound of the formula, $RPO(OR'')_2$, where R is hydrogen or a hydrocarbyl group and R'' is an alkyl group, by means of reaction of that dihalide with the phosphonate at an elevated temperature, e.g., about 120°C–250°C.

16 Claims, No Drawings

PROCESS FOR FORMING PHOSPHONATE POLYMERS

TECHNICAL DESCRIPTION OF THE INVENTION

This invention relates to phosphorus containing polymers and oligomers. More particularly, it relates to a process for making such polymers and oligomers. Hereinafter the term "polymer" will be used to encompass oligomers which are low molecular weight polymers.

Polymers having the repeating unit

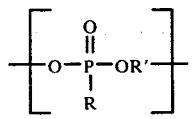

where R is hydrocarbyl, i.e., a radical derived from a hydrocarbon by removal of a hydrogen atom therefrom, preferably $C_1$–$C_4$ alkyl groups, e.g., methyl and ethyl, or hydrogen, and R' is an alkylene group, e.g., a $C_2$–$C_4$ alkylene group, a substituted alkylene group, or an alkylene group having one or more O, S, arylene or vinylene group interruptions in its aliphatic chain, are formed by the process of this invention. These polymers are known and are described in a number of prior art references including U.S. Pat. Nos. 2,893,961 and 3,298,967 and may contain from 2 to 300 or more such repeating units. They are recognized flame retardants. A number of methods have been advocated in the scientific literature for their formation.

The transesterification of ethylene glycol with phosphonic acid esters, e.g. Petrov et al, Chemical Abstracts, 59 4048g (1963) and the transalkylation of bis(2-chloroethyl) methylphosphonates, e.g. Korshak et al, Chemical Abstracts, 52, 1280e (1958) are two examples of reaction schemes originally reported in the foreign scientific literature. The thermal polymerization of 2-methyl-2-oxo-1,3,2-dioxaphosphorane has also been suggested, e.g. by Korshak et al, Chemical Abstracts 51, 14621g (1957), Korshak, J. Polymer Sci., 31 319 (1958) and Shimidzu et al, J. Polymer Sci., B3,871 (1965).

A number of reaction schemes are also suggested in the U.S. patent literature. McManimie, U.S. Pat. No. 2,893,961 mentions the condensation of phosphorus halides, e.g. hydrocarbonphosphonic dichloride, with other organic compounds, e.g. with dihydroxy compounds or olefins. McCormack et al, U.S. Pat. No. 2,891,915 and Mange U.S. Pat. No. 3,578,731 both mention the transesterification reaction of an active hydrogen compound, e.g. a diol, with a phosphonate having the formula $RPO(OR')_2$.

The prior art processes either require the use of phosphonic acid chlorides which are not readily available or are limited in their applicability to certain specified phosphonates, i.e., the bis(2-haloalkyl) phosphonates, as starting materials. Those processes which utilize the phosphoric dichlorides yield hydrochloric acid as a byproduct. This byproduct generally causes side reactions and leads to an undesirably high acid content in the polymeric or oligomeric phosphonate products. The transesterification route of the prior art also shares the fault of giving highly acidic products due to a competing alkylation reaction.

The present invention utilizes the readily available and easily handled dialkyl phosphonates as reactants. These compounds are also relatively stable. The present process also utilizes as a source of the linking group R' between the phosphonate groups of the product, a wide range of readily avilable organic dihalides.

The process of the present invention comprises the reaction of a dihalide of the formula:

$$X - R' - X \qquad (II)$$

wherein R' is an alkylene group, e.g., a $C_2$-$C_4$ alkylene group, a substituted alkylene group, or an alkylene group having O, S, arylene or vinylene group interruption in its aliphatic chain, and X is chlorine or bromine and is attached to the terminal carbon atoms in R', with a phosphonate compound, of the formula $RPO(OR'')_2$ where R is hydrogen or a hydrocarbyl group formed by removal of hydrogen from a hydrocarbon and R'' is an alkyl group, preferably a $C_1$-$C_4$ alkyl group, while the phosphonate is at a reaction temperature of from 120° to 250°C, preferably about 160°C to 200°C. "Hydrocarbyl" as used herein denotes any radicals obtained from aliphatic hydrocarbons, both saturated and unsaturated, from cyclic hydrocarbons or from aromatic hydrocarbons. Representative hydrocarbyl groups are methyl, ethyl, dodecyl, eicosyl, allyl, vinyl, cyclohexyl, cyclopentenyl, butadienyl, phenyl, and halogenated phenyl. The $C_1$-$C_{20}$ hydrocarbyl groups are preferred.

When the dihalide is one which boils below the selected reaction temperature, e.g., ethylene dichloride (the preferred dihalide), ethylene dibromide, 1,3-dichloropropane, 1,3-dibromopropane, 1,4-dichlorobutane, and 1,4-dibromobutane, it must be added dropwise to the phosphonate. The rate of addition of the low boiling dihalide must be quick enough to ensure a rapid reaction but not so quick as to cause the reaction temperature to fall below the desired level.

R' can also be substituted on its non-terminal carbon atoms by halogens, e.g. chloro or bromo, if desired, and can also have its aliphatic chain interrupted with S, O, vinylene or arylene groups. Four such interruptions when vinylene, O and S are utilized are shown below:
—C-C=C-C- or -C-C-O-C-C- or -C-C-S-C-C- or -C-C-O-C-O-C-C-

Some preferred R' groups are: —$CH_2CH_2$—; —$CH_2CHClCH_2$—; —$CH_2CH_2OCH_2OCH_2CH_2$—, —$CH_2CH=CHCH_2$—; —$CH_2C_6H_4OC_6H_4CH_2$—; —$CH_2C(CH_2OH)_2CH_2$—; and —$CH_2C_6H_4CH_2$—. When R' is —$CH_2CH=CHCH_2$— in the initial reaction product, the addition of halogen such as chlorine or bromine affords a product wherein R' is —$CH_2CHXCHXCH_2$—, where X is halogen.

Catalysts which are nucleophiles should be used if a commercially feasible reaction time is intended. The catalyst can be used in an amount ranging from 0.05% to 10% by weight of the reaction mixture, preferably between 0.5% and 1.5%. Preferred catalysts for use are tetraethylammonium hydroxide, tetraethylammonium chloride, sodium carbonate, sodium bicarbonate and lithium chloride. Others which can be used are the alkali metal and alkaline earth compounds conventionally recognized as bases, for example, oxides such as sodium oxide, potassium oxide, magnesium oxide, calcium oxide, and the like; alkali metal and alkaline earth hydroxides, such as sodium hydroxide, potassium hydroxide, magnesium hydroxide, calcium hydroxide, and the like and ammonium hydroxide; the corresponding carbonates and bicarbonates, such as sodium carbonate and bicarbonate, potassium carbonate and bicarbonate, magnesium carbonate and bicarbonate, calcium carbonate, and the like; alkoxides, such as sodium methoxide, potassium ethoxide, magnesium ethoxide, calcium ethoxide, and the like; phenolates, such as sodium phenolate, potassium phenolate, calcium phenolate, and the like; salts of strong bases and weak or volatile acids such as alkali metal and alkaline earth metal acetates, phosphates, chlorides, and bromides; and salts of organic phosphorus acids and partial phosphate esters. Organic bases such as amines, for example, pyridine, quinoline, triethylamine, tetramethylguanidine, N-methylmorpholine, butylamine, aniline, and the like may be used. Additionally, very weak organic bases such as amides, for example N-methylpyrrolidone and hexamethylphosphoric amide, are effective.

The reaction is begun with the addition of the phosphonate reagent, the dihalide (if sufficiently high boiling) and the catalyst to the reaction vessel, the heating of the mixture to the desired reaction temperature, e.g. above 120°C., preferably above 160°C. If the dihalide boils lower than the desired reaction temperature, it must be slowly added to the phosphonate reagent and catalyst. The reaction is continued, under reflux, for a reaction time of 7 to 46 hours, depending upon the reactor configuration, amounts of reagents, and the catalyst level. A preferred reaction time is 12 to 24 hours. The product that results from the reaction may be post-treated with a lower alkyl alcohol, e.g., methanol, ethanol, and the like and then with an alkylene oxide to reduce any undesired residual acidity contained therein. While ethylene oxide and propylene oxide are preferred agents for this post-treatment procedure at levels ranging from 0.05% to 5% by weight of the product, a variety of other mono- and polyepoxides which are known in the art may be used. Other epoxide compounds which can be used are butylene oxide, styrene oxide, epichlorohydrin, epibromohydrin, trichlorobutylene oxide, diglycidyl ether, glycidyl butyl ether, glycidyl alkyl ether, glycidyl ether of phenol, diglycidyl ether of resorcinol, glycidyl ether of cresol and brominated cresol, glycidyl esters of acids such as acetic, arylic and methacrylic acid, glycidol, diglycidyl ethers of bisphenol A and related epoxy resins made from bisphenol, or tetrahalobisphenols and epichlorohydrin, diepoxide of dicyclopentylene ether, the diepoxide of vinylcyclohexene, the diepoxide of cyclohexenylmethyl cyclohexenecarboxylate, the diepoxide of bis-cyclohexenylmethyl adipate, and the like. Similarly, alcohols or polyols other than methanol can be used for this purpose.

The present invention is illustrated using the following Examples:

EXAMPLE 1

A flask was charged with 372g (3.0 moles) of dimethyl methylphosphonate and 5g tetraethylammonium chloride. This was heated until refluxing began at 177°C. Ethylene dichloride (297g, 3.0 moles) was then added dropwise with the temperature being maintained above 160°C. About one-half of the ethylene dichloride was added within 6 hours and 75% had been added after 9 hours. The addition was completed at 20 hours. An aqueous acid number of 10 mg KOH/g was noted. A total of 269g (5.3 moles) of methyl chloride byproduct had collected in a cold trap (−78°C).

Neutralization was accomplished by reacting the product with 15g methanol at 100°C. for 5 hours. Excess alcohol was subsequently stripped under a water aspirator vacuum. Next, ethylene oxide was bubbled into the reaction product for several hours. A water aspirator vacuum strip followed. Obtained were 363g of a clear pale yellow semi-viscous liquid having an aqueous acid number of 0.33 mg KOH/g and OH number of 99.4 mg KOH/g. The phosphorus content was 23.4%.

EXAMPLE 2

A reactor was charged with 186g (1.5 moles) of dimethyl methylphosphonate and 2.5 g of $Na_2CO_3$. The mixture was heated until refluxing began and 148.5g (1.5 moles) of ethylene dichloride were added at a rate sufficient to maintain the temperature at greater than 160°C. in the pot. Methyl chloride volatiles were collected as evolved in a dry ice-acetone trap.

The aqueous acid number of the product was 88 mg KOH/g. Thirty eight grams of methanol were subsequently added to the product, and it was heated at 95°C. for 2 hours. Unreacted methanol was stripped off under a 30 mm vacuum. Ethylene oxide was then bubbled into the product for 2 hours at 100°C. A 30 mm vacuum strip followed. The product was a clear pale yellow semiviscous liquid and weighed 182.9g. The % P was 23.0 while the OH number was 132.5 and the acid number was 1.52 mg KOH/g.

EXAMPLE 3

The reactor was charged with 186g (1.5 moles) of dimethyl methylphosphonate and 2.5g of lithium chloride. One hundred forty-eight and one half grams of ethylene dichloride (1.5 moles) was added dropwise to the solution which was maintained at about 170°C. The ensuing product had an acid number of 111. Ethylene glycol (10g) was added, and the product was heated at 100°C. for 7 hours. Final neutralization was conducted using ethylene oxide at around 100°C. for about 4 hrs. A semi-viscous, clear colorless product weighing 182g was obtained having an acid number of 4.8 mg KOH/g.

EXAMPLE 4

Dimethyl methylphosphonate (186g) and 2.5g of sodium bicarbonate catalyst were added to a vessel equipped with a condenser mounted onto a side arm dropping funnel. Such a reactor design allows a more precise regulation of the dropwise addition of dihalide reagent. It permits excess unreacted dihalide to boil out of the vessel back into the dropping funnel to be recycled. Ethylene dichloride (148.5g) was added dropwise over a 12 hour period while the temperature was maintained at 170°C. to 177°C. A total of 132.8g (2.6 moles) of methyl chloride was recovered as by-product.

The product having an acid number of 107 was treated with methanol (40g) and then was further neutralized with propylene oxide (30g) while at 100°C. A clear, colorless, slightly viscous liquid (189g) remained having an acid number of 5.0.

EXAMPLE 5

Into a reactor were placed 372g (3.0 moles) of dimethyl methylphosphonate and 5g of tetraethylammonium chloride. The mixture was heated till reflux and then 294g (2.0 moles) of 1,2,3-trichloropropane was added dropwise at such a rate as to maintain a pot temperature of greater than 160°C. Within 29 hours a total of 201g (4.0 moles) of methyl chloride were collected in a trap at −78°C. The product was neutralized with methanol and then propylene oxide.

EXAMPLE 6

A mixture of 248g (2.0 moles) of dimethyl methylphosphonate and 3g tetraethylammonium chloride was heated to reflux (177°C.). To this was added dropwise 229g (1.8 moles) of bis (2-chloroethyl) ether over a 3 hour period. During this time, and for a subsequent five hours, 163g (3.2 moles) of methyl chloride was recovered in a cold trap. The product, having an acid number of 26 mg KOH/g. was neutralized with 35g of propylene oxide for 2 hours at 90°C. Volatiles were removed at 90°C. first under a water aspirator vacuum and then by using a wiped film evaporator (0.1 mm). A clear yellow fluid weighing 284.4g was obtained. This material had an acid number of 2.2 mg KOH/g, an OH number of 31.8 mg KOH/g, a phosphorus content of 18.8%, and a chlorine content of 1.2%.

EXAMPLE 7

To a 12 liter reactor was charged 3720g (30 moles) of dimethyl methylphosphonate and 10g anhydrous sodium carbonate. When the mixture had attained reflux, 3597g (25.2 mole) of bis(2-chloroethyl)ether was added dropwise over an 8.5 hour period at a rate consonant with maintaining a 172°–175°C. pot temperature. After a further 8 hour reaction time, a total of 2351g (46.6 mole) of methyl chloride was observed in the by-product cold trap. An acid number of 14.0 mg KOH/g was noted. Neutralization was accomplished by the bubbling-in of ethylene oxide at 100°C. Residual volatiles were removed at 100°C. over 3 hours using a water aspirator vacuum. Obtained were 4,782g of a semi-viscous pale-orange liquid having an acid number of 0.56 mg KOH/g and OH number of 23.4 mg KOH/g. The phosphorus content analyzed as 18.6% and residual chlorine as 2.8%.

EXAMPLE 8–19

The reaction of the present invention was carried out by varying conditions such as catalyst type, catalyst concentration, ethylene dichloride concentration and reaction time. The Table set forth below summarizes the results.

thane, 260g (2.1 moles) of dimethyl methylphosphonate, and 1g of sodium carbonate was heated under reflux condenser at 161–193°C for 7 hours until no further methyl chloride was evolved from the condenser outlet as determined by collection in a dry-ice-cooled trap. Based on weight loss, 4 moles of methyl chloride had been evolved. The product was a viscous water-soluble syrup. When applied to cotton cloth at 20% add-on, (along with 1% zinc nitrate catalyst to provide transacetalization during curing at 150°C. for 3 minutes) a flame retardant finish was obtained.

EXAMPLE 21

A polymer having a repeating unit of the formula $\{OCH_2CH=CHCH_2OP(O)(CH_3)\}$ was formed. A mixture of 250g (2 moles) of 1,4-dichloro-2-butene, 248g (2 moles) of dimethyl methylphosphonate, and 1g of sodium carbonate was heated for 9 hours until methyl chloride evolution ceased. The weight decrease of the reaction mixture was 197g indicating that substantially the theoretical 4 moles (202g.) of methyl chloride had been evolved. The product was a very viscous syrup whose infrared spectrum supported the assigned structure.

EXAMPLE 22

A product having a repeating unit of the formula $\{OCH_2CHBrCHBrCH_2OP(O)(CH_3)\}$ was formed utilizing the product from Example 21. To a solution of 148g of the product of the preceding example, in 1000 ml of methylene chloride, was slowly added 160g of bromine. After the exothermic reaction was completed, the mixture was stripped to 100°C. under vacuum, leaving 307g of product (substantially the theoretical for additive bromination) of a viscous syrup, having 52% Br and 10% P by analysis.

EXAMPLE 23

A polymer having a repeating unit of the formula $(CH_3O)(CH_3)P(O)(OCH_2C_6H_4OC_6H_4CH_2OP(O)(CH_3)(OCH_3)$ was formed.

A mixture of 80g (0.3 mole) of bis(chloromethyl) diphenyl oxide ($ClCH_2C_6H_4OC_6H_4CH_2Cl$), 49.6g (0.4 mole) of dimethyl methylphosphonate and 0.2g sodium carbonate was heated at 161°–195°C for 3 hours until methyl chloride solution was complete to obtain the product as a brownish resin-like solid, effective as a

| Example | Catalyst | Moles of Reactants | Reaction Time (hrs) | Acid No.* (in Methanol) | Post-Treatment | % P | OH No. | Final Acid No. (in Methanol) |
|---|---|---|---|---|---|---|---|---|
| 8 | Et₄NCl | 2 | 14 | 49 | — | — | — | — |
| 9 | Et₄NCl | 3 | 30 | 39 | EtO** | — | — | 2.2 |
| 10 | Et₄NCl | 3 | 27 | 40 | — | — | — | — |
| 11 | Et₄NCl | 3 | 24 | 36 | MeOH, EtO | 23.8 | — | 0.1 |
| 12 | Na₂CO₃(0.2%) | 50 | 43 | 36 | MeOH, EtO | 23.2 | 97 | 0.6 |
| 13 | Et₄NCl(1.3%) | 1.5 | 25 | 46 | MeOH, EtO | — | — | nil |
| 14 | Et₄NCL(1.3%) | 1.5 | 27 | 58 | MeOH, EtO | — | — | nil |
| 15 | Na₂CO₃(8%) | 1.5 | 7.0 | 50 | MeOH, EtO | — | — | nil |
| 16 | Na₂CO₃(1.3%) | 1.5 | 12 | 43 | — | — | — | — |
| 17 | Na₂CO₃(1.3%) | 99 | 23 | 46 | MeOH | 23.1 | 176 | 0.3 |
| 18 | Na₂CO₃(1.3%) | 1.5 | 8.5 | 38 | — | — | — | — |
| 19 | Na₂CO₃(1.3%) | 1.5 | 8.5 | 41 | — | — | — | — |

*The acid number in methanol is roughly one-half the aqueous acid number.
**EtO indicates "ethylene oxide"

EXAMPLE 20

A polymer having a repeating unit of the formula $\{OCH_2CH_2OCH_2CH_2OP(O)(CH_3)\}$ was formed. A mixture of 346g (2 moles) of bis(2-chloroethoxy)meflame retardant char-producing additive in polystyrene at 10% loading.

EXAMPLE 24

Formation of a polymer having the repeating unit $\{OCH_2C(CH_2OH)_2CH_2OP(O)(CH_3)\}$ was performed. A reactor, fitted with condenser, mechanical stirrer thermometer and gas outlet tube leading to a cold trap, was charged with 262g (1.0 mole) of dibromoneopentyl glycol, 124g (1.0 mole) of dimethyl methylphosphonate and 2g of tetraethylammonium chloride. The mixture was heated to and maintained at 180°C. Methyl bromide, totaling 111.9g, was continuously evolved and collected at −78°C over a four hour period. Subsequently, the temperature was lowered to 110°C whereupon 30 ml of propylene was added. The mixture was stirred for 0.5 hour at 110°C and then a water aspirator vacuum was applied to remove volatiles. A clear yellow syrup remained having an acid number of 1.7 mg KOH/g. The product's infrared spectrum exhibited hydroxyl bands at 3430cm$^{-1}$ and the absence of certain fingerprint bands indicative of dimethyl methylphosphonate. The product is an effective flame retardant reactive polyol for use in a urethane formulation at 3–10 parts per hundred of polyol.

EXAMPLE 25

Formation of a polymer having the repeating unit $\{OCH_2C(CH_2OH)_2CH_2OP(O)(CH_3)\}$ was formed. The reactor was charged with 131g (0.5 mole) of dibromoneopentyl glycol, 124g (1.0 mole) of dimethyl methylphosphonate and 2g of tetraethylammonium chloride. The mixture was heated to and maintained at 170°–180°C. A total of 106.6g methyl bromide was evolved and collected in a cold trap, attached to the reactor, over a five hour period. Subsequently, the reaction mixture was cooled to 110°C and 30 ml of propylene oxide was added. After an hour at 110°C, the product was stripped of volatiles under vacuum. A clear yellow syrup was obtained with an acid number of 30 mg KOH/g.

The above products are useful as flame retardants for incorporation into polymer systems such as polyurethanes, polyesters, epoxies, aminoplasts, furan resins, phenolics, and vinyls in the form of castings, moldings, laminates, foams, films, coatings, or fibers. Levels of 1 to 40% are useable, more typically 3 to 30% depending on the substrate.

EXAMPLE 26

The product of Example 1 is admixed with an uncured melamine-formaldehyde resin at the level of 10 parts of the phosphorus product per 100 parts of resin solids. The liquid resin-flame retardant mixture is then used to impregnate paper to the level of 1 part by weight of resin per part of paper. The paper after drying is fabricated into an automotive air filter and cured at 160°C. for 5 minutes. The resultant paper-resin composite is self-extinguishing when ignited.

What is claimed:

1. A process for preparing polymers containing the repeating unit

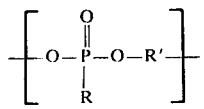

where R is selected from the group consisting of hydrogen and hydrocarbyl and R' selected from the group consisting of alkylene, substituted alkylene and alkylene groups having at least one O, S, arylene, or vinylene interruption therein which comprises the transalkylation at elevated temperature of a dihalide of the formula

X-R'-X where R' has the same meaning given above and X is selected from the group consisting of chlorine and bromine and is attached to the terminal carbon atoms in R', with a phosphonate having the formula RPO(OR'')$_2$ where R is as defined above and R'' is an alkyl group.

2. A process as claimed in claim 1 wherein the transalkylation is carried out at about 120°C to 250°C.

3. A process as claimed in claim 1 where the transalkylation is carried out at about 160°C. to 200°C.

4. A process as claimed in claim 1 wherein a catalyst is also present in an amount ranging from about 0.05 to 10% by weight.

5. A process as claimed in claim 4 wherein the amount of catalyst ranges between about 0.5 to 1.5% by weight.

6. A process as claimed in claim 4 wherein the catalyst is selected from the group consisting of the alkali metal and alkaline earth oxides, hydroxides, carbonates, bicarbonates, alkoxides, phenolates, the salts of strong bases and weak volatile acids, the salts of organic phosphorus acids and partial phosphate esters, organic amines and organic amides.

7. A process as set forth in claim 1 wherein the dihalide boils lower than the transalkylation temperature and is added slowly to the phosphonate.

8. A process as set forth in claim 1 wherein the dihalide compound is selected from the group consisting of ethylene dichloride and ethylene dibromide.

9. A process as claimed in claim 8 wherein the dihalide compound is ethylene dichloride.

10. A process as set forth in claim 9 wherein the reaction temperature is maintained between 160°C. and 200°C. during the course of the reaction.

11. A process as claimed in claim 1 wherein R' is an alkylene group which is substituted with a halogen.

12. A process as claimed in claim 1 wherein R' has a structure selected from the group consisting of -C-C=C-C-; -C-C-O-C-C-; and -C-C-S-C-C-.

13. A process as claimed in claim 1 wherein R' is selected from the group consisting of —CH$_2$CH$_2$-, —CH$_2$CHClCH$_2$—; —CH$_2$CH$_2$OCH$_2$OCH$_2$CH$_2$—; —CH$_2$CH=CHCH$_2$—; —CH$_2$CHBrCHBrCH$_2$—; —CH$_2$C$_6$H$_4$OC$_6$H$_4$CH$_2$—; —CH$_2$C(CH$_2$OH)$_2$CH$_2$—; and —CH$_2$C$_6$H$_4$CH$_2$—.

14. A process as claimed in claim 1 wherein the polymer is post treated with a lower alkyl alcohol and an alkylene oxide to reduce residual acidity.

15. A process as claimed in claim 1 wherein the hydrocarbyl group is a C$_1$-C$_{20}$ hydrocarbyl group.

16. A process as claimed in claim 1 wherein R'' is a C$_1$ - C$_4$ alkyl group.

* * * * *